(12) United States Patent
Eigenbrodt et al.

(10) Patent No.: US 7,223,784 B2
(45) Date of Patent: May 29, 2007

(54) COMPOUNDS FOR THE MODULATION OF THE GLYCOLYSIS ENZYME AND/OR TRANSAMINASE COMPLEX

(75) Inventors: Erich Eigenbrodt, Linden (DE); Hans Scheefers, Wettenberg-Wissmar (DE); Sybille Mazurek, Linden (DE)

(73) Assignee: ScheBo® Biotech AG, Giessen (DE)

( * ) Notice: Subject to any disclaimer, the term of this patent is extended or adjusted under 35 U.S.C. 154(b) by 79 days.

(21) Appl. No.: 10/618,578

(22) Filed: Jul. 11, 2003

(65) Prior Publication Data

US 2004/0147587 A1 Jul. 29, 2004

(30) Foreign Application Priority Data

| Sep. 6, 2002 | (DE) | ................................ 102 44 080 |
| Sep. 11, 2002 | (DE) | ................................ 102 42 445 |
| Sep. 23, 2002 | (DE) | ................................ 102 44 299 |

(51) Int. Cl.
*A61K 31/40* (2006.01)
*A61K 31/21* (2006.01)
*A61K 31/275* (2006.01)
*C07D 209/48* (2006.01)
*C07C 271/02* (2006.01)

(52) U.S. Cl. ...................... 514/417; 514/506; 514/528; 548/479; 560/160

(58) Field of Classification Search ................ 548/479; 560/160; 514/417, 506, 528
See application file for complete search history.

(56) References Cited

FOREIGN PATENT DOCUMENTS

| DE | 198 57009 A1 | 6/2000 |
| WO | WO 99/54286 | 10/1999 |

OTHER PUBLICATIONS

Eigenbrodt, E.; Gerbracht, U; Mazurek, S.; Presek, P.; Frus, R. "Carbohydrate Metabolism and Neoplasia: New Perspectives for Diagnosis and Therapy". Biochemical and Molecular Aspects of Selected Cancers. Chapter 10. vol. 2. pp. 311-385. 1994.
Kauppinen, Risto A.; Sihra, Talvinder S.; Nicholls, David G. "Aminooxyacetic acid inhibits the malate-aspartate shuttle in isolated nerve terminals and prevents the mitochondria from utilizing glycolytic substrates". Elsevier Science Publishers (Biomedical Division). vol. 930. 1987. pp. 173-178.
Tomasiak, Marian. "The Importance of Aspartate Aminotransferase for Platelet Aggregation". Haematologia. vol. 19. No. 2. 1986. pp. 101-112.
Tomasiak, Marian, "Importance of the malate-aspartate shuttle for the reoxidation of glycolytically produced nadh and for cell aggregation in procine blood platelets". Aeta Biochemica Polonila. vol. 34. No. 3. 1987. pp. 269-284.

*Primary Examiner*—Kamal A. Saeed
*Assistant Examiner*—Ebenezer Sackey
(74) *Attorney, Agent, or Firm*—Mayer & Williams PC; Keum J. Park, Esq.; Karin L. Williams, Esq.

(57) ABSTRACT

The invention relates to compounds for the modulation of the glycolysis enzyme complex and of the transaminase complex, pharmaceutical compositions containing such compounds as well as uses of such compounds for preparing pharmaceutical compositions for treating various diseases.

12 Claims, 10 Drawing Sheets

US 7,223,784 B2

COMPOUNDS FOR THE MODULATION OF THE GLYCOLYSIS ENZYME AND/OR TRANSAMINASE COMPLEX

FIELD OF THE INVENTION

The invention relates to compounds for the modulation of the glycolysis enzyme and/or transaminase complex and thus in particular to the growth inhibition of cells and/or bacteria, pharmaceutical compositions containing such compounds as well as uses of such compounds for preparing pharmaceutical compositions for treating various diseases.

BACKGROUND OF THE INVENTION

Cancer is one of the most frequent causes of death today, and the number of cancer cases in industrialized countries continuously grows. This is mainly based on the fact that malignant tumors are a disease of higher age, and due to a successful controlling of infection diseases, more people will reach this age. In spite of all progress in the diagnostic and therapeutic field, the healing chances for most frequent inner cancer types are seldom higher than 20%. A cancerous tumor nowadays can be destroyed or inhibited in its growth. A re-conversion of a tumor cell into a normal cell is, however, not yet possible. The most important therapeutic measures, the operation and the irradiation, remove cancer cells from the organism. The presently used chemotherapeutic agents of the for cancer, the cytostatics, also lead to a destruction or damaging of tumor cells only. In most cases the effect is so non-specific that simultaneous heavy damage to healthy cells will occur.

In general, tumor cells have a metabolism differing from healthy cells, in particular glycolysis. Thus, a change of the isoenzyme system involved in the glycolysis and a change of the transport of NADH is typical for tumor cells. Among other effects, the activity of the enzymes of the glycolysis is increased. This permits high reaction rates under the aerobic conditions typical for tumor cells. For details, reference is made to E. Eigenbrodt et al., Biochemical and Molecular Aspects of Selected Cancers, Vo. 2, p. 311 ff, 1994.

Various other diseases mentioned below are either characterized by an (excessive) metabolism by the glycolysis enzyme complex and can be treated by the reduction or inhibition thereof.

PRIOR ART

From the document E. Eigenbrodt et al., Biochemical and Molecular Aspects of Selected Cancers, Vo. 2, p. 311 ff, 1994 it is known that glucose analogs are used for inhibiting the glycolysis. Other approaches known herefrom are the use of inhibitors of glycolytical isoenzymes, for instance by suitable chelation or inhibition of chelations. As a result, the tumor cells are so to speak starved out. It is a problem with the above compounds that many of them are genotoxic and/or not sufficiently specific for tumor cells.

SUMMARY OF THE INVENTION

It is the technical object of the present invention to specify active ingredients that are able to modulate or inhibit the glycolysis enzyme and transaminase complex, in particular the proliferation of cancer cells and to thus inhibit the growth of neoplastic tumors as well as defense over-reactions of the body, such as septic shock, autoimmune diseases, transplant rejections as well as acute and chronic inflammatory diseases, and that simultaneously with only slight to no cytoxicity at all with regard to cells having an intact glycolysis enzyme complex or other complex structures. In addition, it is intended to inhibit the growth of unicellular organisms.

DETAILED DESCRIPTION OF THE INVENTION

Figure 1A:
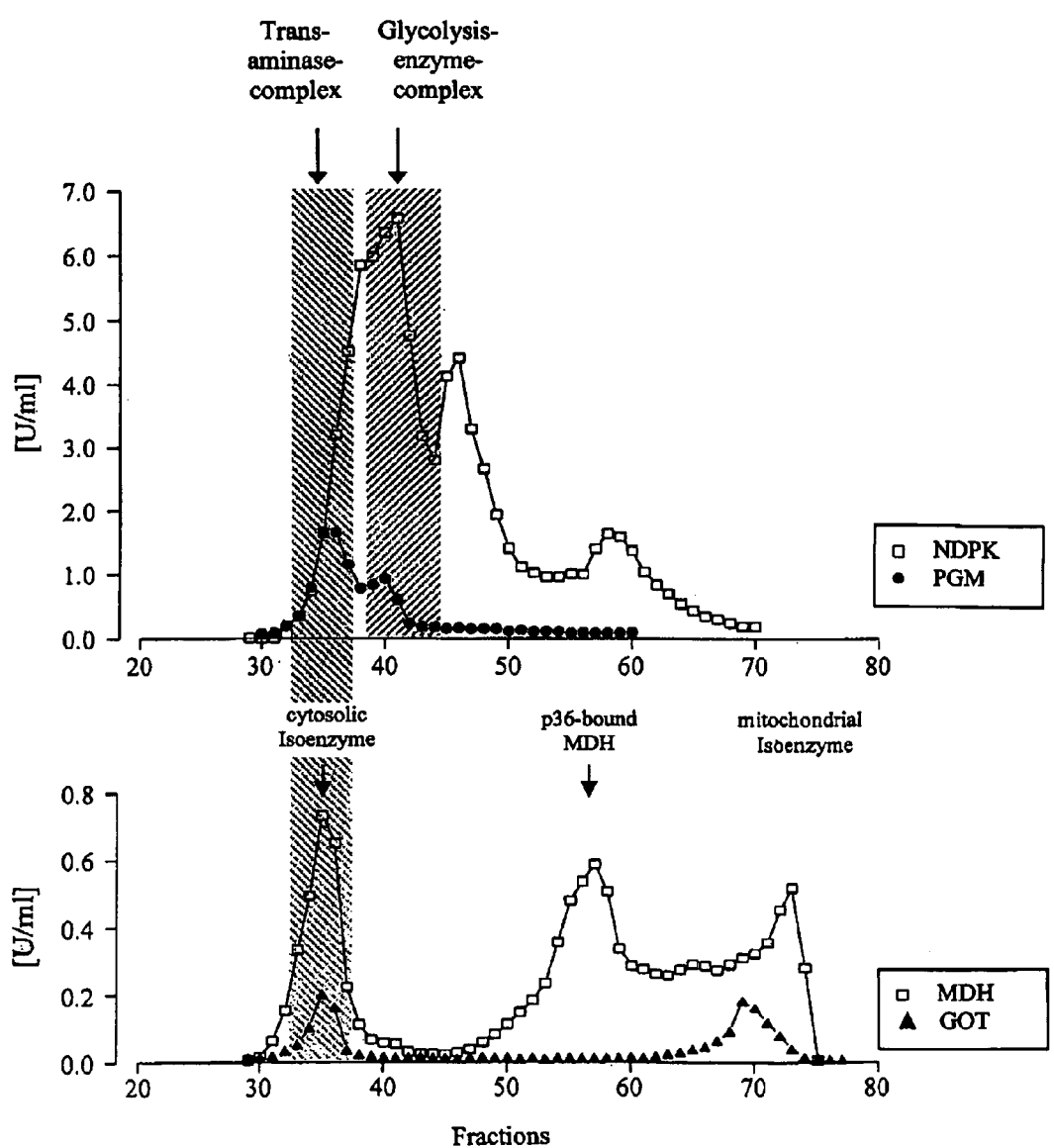
FIG. 1a is a graphical representation showing the migration of PGM from the glycolysis enzyme complex into the transaminase complex.

For achieving said technical object, the invention teaches a compound according to formula I

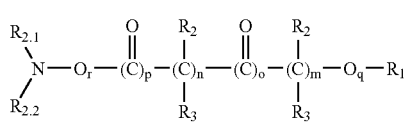

wherein R1=—H, —CN, —COO+, —COS+, —COOH, —COSH, —COOR1.1, —COSR1.1, N-phthalimidyl, wherein R1.1=—H, C1–10 alkyl, C1–10 aralkyl or aryl, wherein R2=—H, C1–C4 alkyl, —OR1.1, -Hal (—F, —Cl, —Br, -J), —NR2.1R2.2, —Am, —O—Am, —S—Am, wherein R3=—H, C1–C4 alkyl, —OR1.1, -Hal (—F—Cl, —Br, -J), —NR2.1R2.2, —Am, —O—Am, —S—Am, wherein R2.1=—H, C1–10 alkyl, C1–10 aralkyl or aryl, wherein R2.2=—H, C1–10 alkyl, C1–10 aralkyl or aryl, wherein R2.1 and R2.2 may be identical or different, wherein n and m may be identical or different and 0 to 10, wherein o and p may be identical or different and 0 to 3, wherein o>0, if n and m=0, wherein R2 and R3 may be identical or different for Cn and/or Cm, wherein R2 may be identical or different for every Cx=1 . . . n, wherein R3 may be identical or different for every Cy=1 . . . m, wherein —Am is an amino acid radical, wherein q and r=0 or 1 and identical or different, wherein —$O_r$— and/or —$O_q$— may also be replaced by —$S_r$— or —$S_q$—, resp., wherein —NR2.1R2.2 may be replaced by a linear or branched —C1–C20 alkyl, aralkyl or aryl, wherein a group —CN, —(CO)—CN, —(CO)—O—R1 or —(CO)—R1 or —C—O—R1 may be replaced by —$SO_2$—NR2.1R2.2, or a physiologically well tolerated salt of such a compound.

An amino acid radical is defined in an amino acid as follows: $NH_2$—CHAm—COOH. These are in particular amino acid radicals of the proteinogenic amino acids, especially of the essential amino acids. As far as a compound according to the invention has an optical activity (for instance according to embodiments of claim 3), the various variants such as L and D types are also included. Corresponding considerations apply in the case of (several) chiral centers.

Particularly suited are compounds according to the invention, wherein R2 exists at least singly as —Am, wherein —Am preferably represents an amino acid radical of an essential amino acid, wherein in particular q=0 and r=1 or q=1 and r=0 or q=1 and r=1m=1, R3=—H, n=o=p=0, R2.1=R2.2=—H.

Further, various specific groups are preferred, namely: i) wherein n=o=p=0, wherein m=0 to 4, wherein R2=R3=—H, wherein R2.1=R2.2=—H, wherein q=0 and r=1, ii) wherein m=p=0, wherein o=1, wherein n=0 to 4, wherein R2=H, wherein R3=—H or -Hal in the case Cx=1, wherein R3=—H for all Cx=n>1, wherein R2.1=R2.2=—H, wherein q=0 and r=1, iii) wherein m=1 to 4, wherein n=o=p=0, wherein R2=H, wherein R3=—H or -Hal in the case Cy=1, wherein R3=—H for all Cy=m>1, wherein R2.1=R2.2=—H, wherein q=0 and r=1, iv) wherein o=p=1, wherein m=0, wherein n=0 to 4, wherein R2=R3=—H, wherein R2.1=R2.2=—H, wherein q=0 and r=1, v) wherein n=p=0, wherein o=1, wherein m=0 to 4, wherein R2=R3=—H, wherein R2.1=R2.2=—H, wherein q=0 and r=1, or vi) wherein m=p=0, wherein o=1, wherein n=1 to 4, wherein R2=R3=—H, wherein R2.1=R2.2=—H, wherein q=0 and r=1.

Generally, one R2 may be replaced by —Am.

Examples for compounds wherein —NR2.1R2.2 is replaced by —C1–C20 alkyl are: $CH_3$—O—$(CH_2)_m$—R1, $CH_3$—O—CO—$(CH_2)_m$—R1, CR5R6R7—O—$(CH_2)_m$—R1, CR5R6R7—O—CO—$(CH_2)_m$—R1, wherein R5, R6 and R7 may be —C1–C10 alkyl, linear or branched, not substituted or substituted. ($CH_2$) may of course also be (CR2R3). —O— or =O may be replaced by —S— or =S. R1 is as specified above. CR5R6R7 may in particular be t-butyl.

Examples for the compounds according to the invention are: $NH_2$—O—$(CH_2)_m$—R1, $NH_2$—O—$(CH_2)_n$—CO—R1, $NH_2$—O—CHHal-$(CO)_o$—R1, $NH_2$—O—CHHal-$CH_2$—$(CO)_o$—R1, $NH_2$—O—CHHal-$(CH_2)_2$—$(CO)_o$—R1, $NH_2$—O—CHHal-$(CH_2)_3$—$(CO)_o$—R1, $NH_2$—O—CHHal-$(CH_2)_4$—$(CO)_o$—R1, $NH_2$—O—CO—$(CH_2)_n$—CO—R1, $NH_2$—O—CO—$(CH_2)_n$—R1, $NH_2$—O—$(CH_2)_n$—CO—R1, $NH_2$—O—CO—$(CH_2)_n$—$CHNH_2$—R1, $NH_2$—O—$(CH_2)_n$—$CHNH_2$—R1, with R1=—CN or —COOH, m or n=0 to 4, o=0 or 1, wherein —O— may be replaced by S.

Another formula according to the invention is formula II

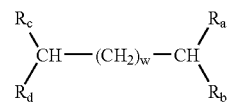

wherein $R_a$=—CN, $R_b$=—H, =O, —OH, —$NH_2$, $R_c$=—$NH_2$, —O—$NH_2$, —O—(C1–10)alkyl, $R_d$=—H, -Hal, =O, —OH, wherein the case of =OH the one CH is omitted, wherein w=0 to 10, e.g. 1 to 4.

Another formula according to the invention is formula III

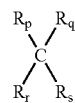

wherein Rp=—R1, —O—R1, —O—$(CR2R3)_x$—R1, —$(CR2R3)_x$—O—R1, $R_q$=—NR2.1R2.2, —O—NR2.1R2.2, —O—$(CR2R3)_x$—NR2.1R2.2, —$(CR2R3)_x$—O—NR2.1R2.2, $R_r$=—Am, —O—Am, —O—$(CR2R3)_x$—Am, —$(CR2R3)_x$—O—Am, —$R_s$=—H, —C1–C10 alkyl, aryl or aralkyl, —C1–C10 hydroxyalkyl, aryl or aralkyl, or an ether of such a hydroxy radical, wherein —O— may be replaced by —S— and x=1 to 10, in particular 1 to 4. R1 is as specified above, in particular —CN or —COOH. Examples of such compounds are: $NH_2$—O—CHAm—R1, $NH_2$—CHAm—O—R1, $NH_2$—O—

CHAm—O—R1, NH$_2$—CHR1—O—Am, Am—O—CHNH$_2$—O—R1, NH$_2$—O—(Am—O—CH—O—R1). On one side of one —O— or several —O— or on both sides of one —O— or several —O— immediately —(CH$_2$)$_x$— may be interposed.

Compounds according to the invention may be present in an ionized condition in a solution, depending on the pH value (e.g. as —COO$^-$ in basic condition or —NH$_3^+$ in acid condition). Salts, such as hydrochlorides, may also be formed.

The invention is based on the finding that beside the classic metabolic diseases, such as diabetes mellitus, adiposity, other diseases, too, such as cancer, autoimmune diseases and rheumatism are caused by metabolic defects. This explains the strong influence of the food on these diseases. A directly measurable biochemical parameter for these metabolic ketoacidoses is the increase of pyruvate kinase type M2 (M2-PK) growing in the blood of all diseases above and below. Depending on the respective disease, the M2-PK detectable in the blood of the patients originates from different cells: for cancer from tumor cells, for sepsis from immune cells, for rheumatism from immune and/or synovial cells. In healthy cells, there are tetrameric forms of the M2-PK in a high-order cytosolic complex, the glycolysis enzyme complex. By the over-activation of oncoproteins, there is an emigration of the M2-PK out of the complex and the typical changes in the tumor metabolism. Simultaneously, the phosphoglyceromutase (PGM) leaves the complex and migrates into another enzyme complex, where the cytosolic transaminases are associated (see example 2). This complex is therefore called transaminase complex. The substrate of the PGM, glycerate-3-P, is the first stage for the synthesis of the amino acids serine and glycine. Both amino acids are essential for the DNA and polypholipid synthesis. By the immigration of the PGM into the transaminase complex, the synthesis of serine from glutamate and thus the glutaminolysis is activated. The same changes take place in immune cells, if the immune system fails, such as for instance in the case of rheumatism, sepsis or polytrauma. The integration of the metabolism of different cells in multi-cellular organisms takes place by organ-specific association of the enzymes in the cytosol: in the muscle for instance by association with contraction proteins. For this reason, the different organs are provided with respectively specific isoenzymes. The dissolution of this order will necessarily lead to diseases. Uni-cellular organisms, such as bacteria or yeasts reacting on a sufficient offer of food with dissipated proliferation, do not have a complex organization of the cytosol. As a consequence, substances inhibiting the failing metabolism of multi-cellular organisms, will also inhibit the proliferation of such uni-cellular organisms.

The invention further teaches the use of a compound according to the invention for preparing pharmaceutical compositions for treating one or several diseases of the group comprising "cancer, chronic inflammations, asthma, arthritis, osteoarthritis, chronic polyarthritis, rheumatic arthritis, inflammatory bowel disease, degenerative joint diseases, rheumatic diseases with cartilage disorders, sepsis, autoimmune diseases, type I diabetes, Hashimoto thyroiditis, autoimmune thrombocytopenia, multiple sclerosis, myasthenia gravis, chronically inflammatory intestinal diseases, Crohn's disease, uveitis, psoriasis, collagenosis, Goodpasture syndrome, diseases with disturbed leukocyte adhesion, cachexia, diseases by increased TNF-alpha concentration, diabetes, adiposity, bacterial infections, in particular with resistant bacteria". The term treatment also comprises prophylaxis.

The invention further teaches a pharmaceutical composition, wherein a compound according to the invention is mixed with one or several physiologically well tolerated auxiliary substances and/or carrier substances and galenically prepared for the local or systemic administration, in particular oral, parenteral, for the infusion into a target organ, for the injection (e.g. IV, IM, intracapsular or intralumbal), for the application in tooth pockets (space between tooth root and gum).

The invention finally teaches the use of a compound according to the invention for inhibiting in vitro the glycolysis enzyme complex, in particular of pyruvate kinase, asparaginase, serine dehydratases, transaminases, desaminases and/or glutaminases. In particular, the transamination, the oxidative deamination, the hydrolytic deamination, the eliminating deamination, and the reductive deamination are blocked.

It is understood that if applicable, there may exist stereoisomers for the compounds according to formula I, such stereoisomers all being covered by the invention. The term alkyl comprises linear and branched alkyl groups as well as cycloalkyl, if applicable also cycloalkyl groups having linear or branched alkyl substituents. The term aryl also comprises aralkyl groups, and alkyl substituents may be alkyl or cycloalkyl.

Surprisingly it has been found that compounds according to the invention are able to competitively inhibit the above members of the glycolysis enzyme complex. The proliferation of cancer cells in therapeutically relevant concentrations can be inhibited. There are no cytotoxic effects to be expected in the respective dosage range. Because of their pharmacological properties the compounds according to the invention are also excellently suitable for the treatment and prophylaxis of the above further diseases. In conjunction with the indications for the inhibition of inflammations or anti-rheumatic effects, it is of a special relevance that the substances according to the invention are non-steroidal substances.

The inhibition of the glycolysis enzyme and of the transaminase complex in particular comprises the inhibition of the metabolic activity and the energy gain from serine, glutamine, ornithine, proline and arginine or from other amino acids of this and other families, but also the synthesis of such amino acids used for energy generation; important energy sources for instance in tumor cells, but also in bacteria and yeasts. The cells or bacteria or yeasts are so to speak starved out. In detail, substances according to the invention block for instance the following reactions: i) threonine to glycine, ii) threonine to α-amino-β-ketobutyrate, iii) α-amino-β-ketobutyrate to glycine, iv) serine pyridoxalphosphate (PLP) Schiffs base to aminoacrylate, in particular folic acid-dependent serine hydroxymethyltransferase, v) aminoacrylate to pyruvate (by displacement of the balance of the natural hydrolysis of the PLP Schiff's base to the Schiffs base), vi) transamination by means of PLP for the synthesis of an amino acid from an oxo acid, in particular of the branch-chained transaminase, the α-ketoglutarate, oxalacetate, 3-hydropyruvate and glyoxalate transaminase, the glutamate dehydrogenase. In particular, the formation of pyruvate from amino acids is inhibited by substances according to the invention. Important is the release of NH$_2$—OH or CH3-OH (—H to —C or —N if applicable replaced by other radicals, for instance alkyl) by glutaminase, arginase, asparaginase or serine hydroxymethyltransferase. This will lead to an increased specificity, since a feature of tumor cells is a high glutaminase and serine hydroxymethyltransferase activity. $NH_2$—OH (hydroxylamine, HA) for instance can be phosphorylated by the high pyruvate kinase activities instead of the —OH of the phosphate (e.g. of the ADP). This will lead to a decoupling of the pyruvate kinase reaction in tumor cells. Therefore, the invention in all generality also comprises all natural metabolites of the substances according to the invention, in particular of the aminooxyacetate, i.e. fractions of these substances.

In the transaminase complex, in addition to the PGM and NDPK, the cytosolic isoforms of the glutamate oxalacetate transaminase (GOT), glutamate pyruvate transaminase (GPT), glutamate dehydrogenase (GlDH) and malate dehydrogenase (MDH) are associated. GOT and MDH are components of the malate-aspartate shuttle, by which the hydrogen produced in the cytosol is transported into the mitochondria. NAD+ is recycled for the cytosolic glyceraldehyde 3-phosphate dehydrogenase reaction. The malate-aspartate shuttle is part of the glutaminolysis. For an active malate-aspartate shuttle, in addition to GOT, the presence of the p36-bound form of the MDH is important, as represented in example 3.

Various further embodiments of the invention are possible. For instance, a pharmaceutical composition according to the invention may comprise several different compounds of the above definitions. Furthermore, a pharmaceutical composition according to the invention may in addition comprise an active ingredient being different from the compound of formula I. Then it is a combination preparation. Therein, the various employed active ingredients may be prepared in a single type of administration, i.e. the active ingredients are mixed in the type of administration. It is however also possible to prepare the various active ingredients in spatially separated types of administration of identical or different species.

As counterions for ionic compounds according to formula I $Na^+$, K+, Li+, cyclohexylammonium or basic amino acids (e.g. lysine, argini, ornithine, glutamine) can be used.

Drugs prepared by the method according to the invention may be administered in an oral, intramuscular, periarticular, intraarticular, intravenous, intraperitoneal, subcutaneous or rectal manner.

The invention also relates to methods for preparing drugs which are characterized by that at least one compound of formula I is brought into a suitable dosage form by using a pharmaceutically suitable and physiologically well tolerated carrier and if applicable further suitable active ingredients, or any additional or auxiliary substances.

Suitable solid or liquid dosage forms are for instance granulates, powders, dragées, tablets, (micro) capsules, suppositories, syrups, juices, suspensions, emulsions, drops or injectable solutions as well as preparations with protracted release of the active ingredient, for the preparation of which usual means such as carrier substances, explosion, binding, coating, swelling, sliding or lubricating agents, flavoring substances, sweeteners and solution mediators are used.

Auxiliary substances are for instance magnesium carbonate, titanium dioxide, lactose, mannite and other sugars, talcum, milk protein, gelatin, starch, cellulose and its derivatives, animal and plant oils such as cod-liver oil, sunflower, peanut or sesame oil, polyethylene glycols and solvents, such as sterile water and one or poly-valent alcohols, e.g. glycerin.

Preferably the drugs are prepared and administered in dosage units, each unit containing as an active component a defined dose of the compound according to formula I of the invention. With solid dosage units such as tablets, capsules, dragées or suppositories, this dose may be 1 to 1,000 mg, preferably 50 to 300 mg, and for injection solutions in an ampule form 0.3 to 300 mg, preferably 10 to 100 mg.

For treating an adult patient of 50 to 100 kg weight, for instance 70 kg, for instance daily doses of 20 to 1,000 mg active ingredient, preferably 100 to 500 mg, are indicated. Under certain circumstances, higher or lower daily doses may be recommendable. The administration of the daily dose may be a one-time administration in the form of a single dosage unit or several smaller dosage units as well as a multi-administration of separated doses in certain intervals.

In the following, the invention is explained in more detail with reference to examples representing embodiments only.

EXAMPLE 1

Quantification of the Effectivity of a Compound According to the Invention

Suitable Novikoff hepatoma cells are obtainable from the tumor bank of the Deutsches Krebsforschungszentrum, Heidelberg (Cancer Research 1951, 17, 1010). 100,000 cells each are sown out per 25 $cm^2$ cultivation bottle. A substance according to the invention, dissolved in a solvent suitable for use in cell cultures, for instance water, diluted ethanol, dimethylsulfoxide or the like, is added in an increasing concentration to the culture medium, e.g. in a concentration range of 80 $\mu M$–5,000 $\mu M$ or of 100 $\mu M$–300 $\mu M$. After four days of cultivation, the number of cells per bottle is counted. In comparison to the control sample (without addition of a compound according to the invention but instead with addition of a reference compound), the measure and the dose dependence of a proliferation inhibition of the used compound can be seen.

EXAMPLE 2

Emigration of the PGM

In FIG. 1a is shown an isoelectric focusing of a tumor cell extract (MCF-7 cells). It can be seen that PGM leaves the glycolysis enzyme complex and migrates into a complex associated with the cytosolic transaminases, the transaminase complex. The transaminase complex is built up as follows: cytosolic glutamate oxalacetate transaminase (GOT), c-malate dehydrogenase (MDH), phosphoglyceromutase (PGM). Not shown are: c-glutamate pyruvate transaminase (GPT), c-glutamate hydroxypyruvate transaminase, c-alanine hydroxypyruvate transaminase, c-serine hydroxymethyl transferase and c-glutamate dehydrogenase (GIDH). The PGM and the nucleotide diphosphate kinase (NDPK) may be associated in the transaminase as well as in the glycolysis enzyme complex.

EXAMPLE 3

Inhibition of the Malate-Aspartate Shuttle

Figure 1B:
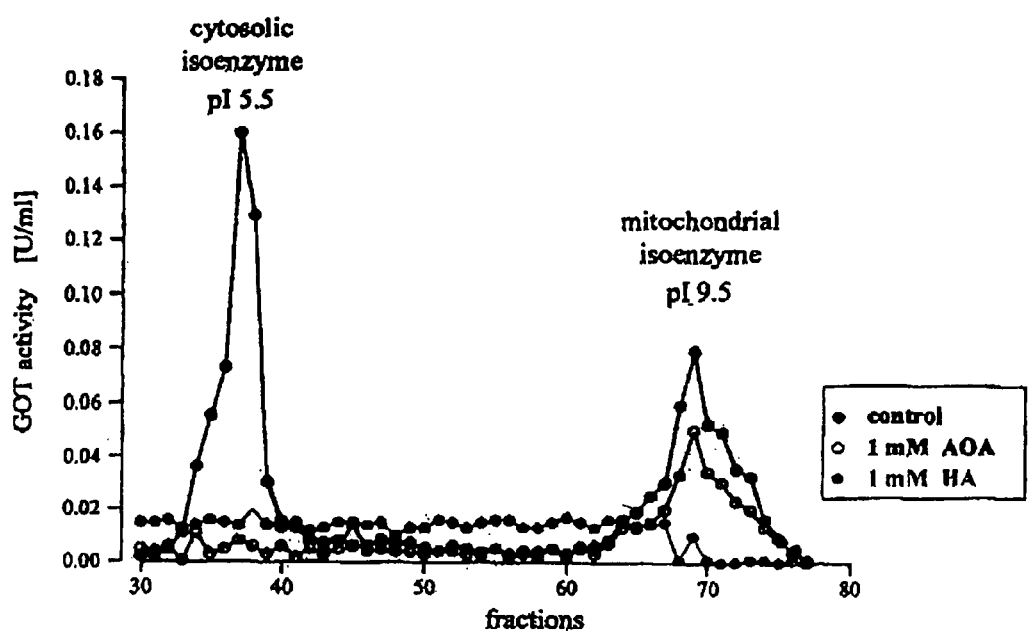
FIG. 1b is a graphical representation showing the effect of arminoacetate (AOA) and hydroxylamine (HA) on the activity of the cytosolic and mitochondrial isoenzyme of the GOT in vitro.

In FIG. 1b is shown the effect of aminoacetate (AOA) and hydroxylamine (HA) on the activity of the cytosolic and mitochondrial isoenzyme of the GOT in vitro. The isoenzymes of the GOT were dissociated by an isoelectric focusing. It can be seen that aminooxyacetate mainly inhibits the cytosolic isoenzyme, and hydroxylamine inhibits both isoenzymes of the GOT. The inhibition of the GOT leads to an inhibition of the malate-aspartate shuttle. As a consequence, NAD cannot be recycled, and the glycolysis is inhibited at the stage of the GAPDH.

Figure 2A:
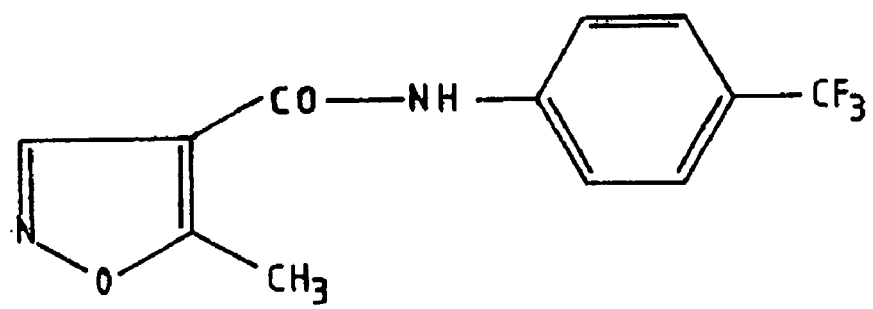
FIG. 2a is the structural formula of 5-methyl-N-[4-(trifluoromethyl)phenyl]isoxazole-4-carboxamide.
Figure 2B:
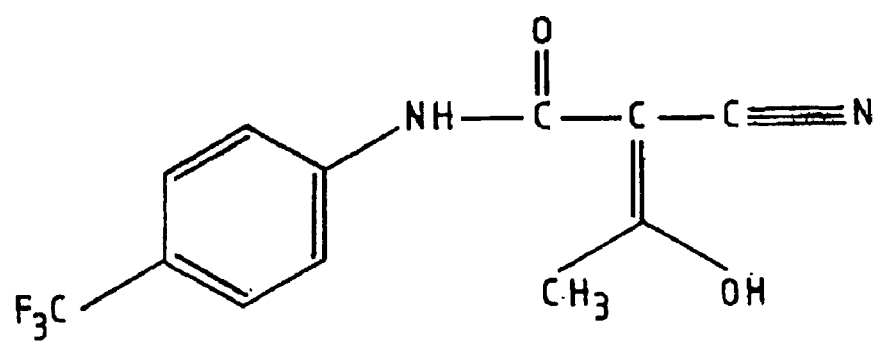
FIG. 2b is the structural formula of (2Z)-2-cyano-3-hydroxy-N-[4-(trifluoromethyl)phenyl]but-2-enamide.
Figure 2C:
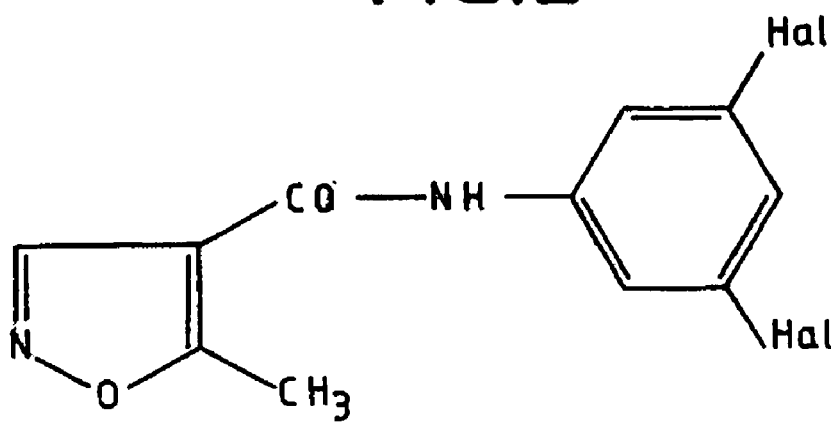
FIG. 2c is the structural formula of N-(3,5-dihalogenophenyl)-5-methylisOxazole-4-carboxamide.
Figure 2D:
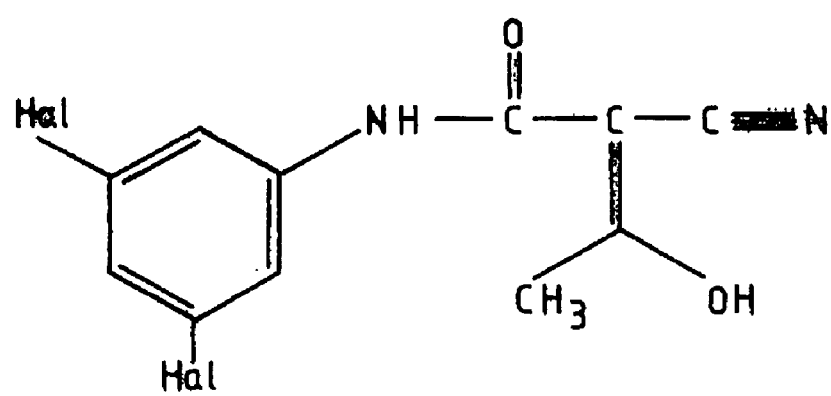
FIG. 2d is the structural formula (2Z)-2-cyano-N-(3,5-dihalogenophenyl)-3-hydroxybUt-2-enamide.
Figure 2E:
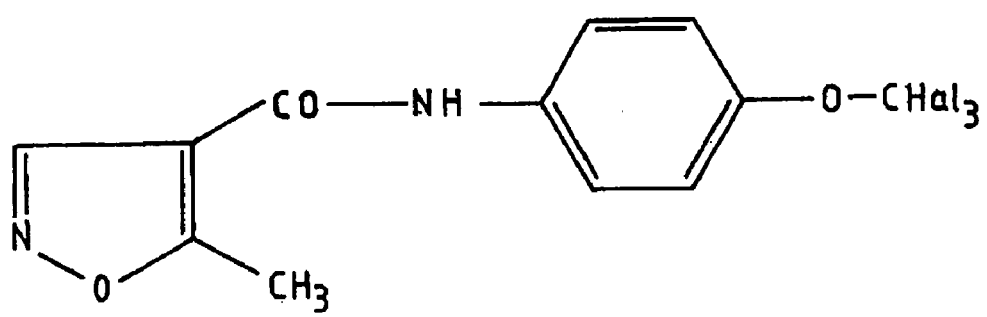
FIG. 2e is the structural formula of 5-methyl-N-[4-(trihalogenomethoxy)phenyl]isoxazole-4-carboxamide.
Figure 2F:
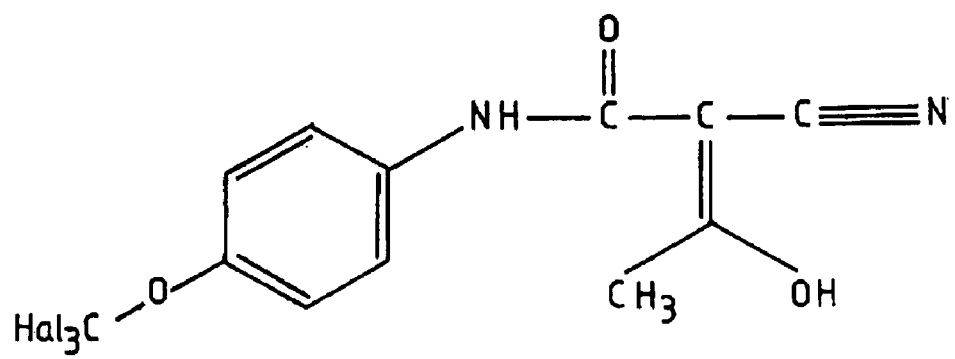
FIG. 2f is the structural formula of (2Z)-2-cyano-3-hydroxy-N-[4-(trihalogenomethoxy)phenyl]but-2-enamide.
Figure 2G:
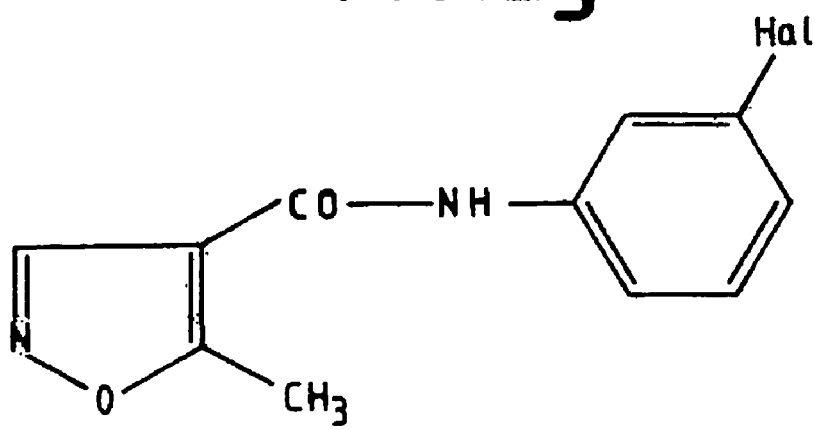
FIG. 2g is the structural formula of N-(3-halogenophenyl)-5-methylisoxazole-4-carboxamide.
Figure 2H:
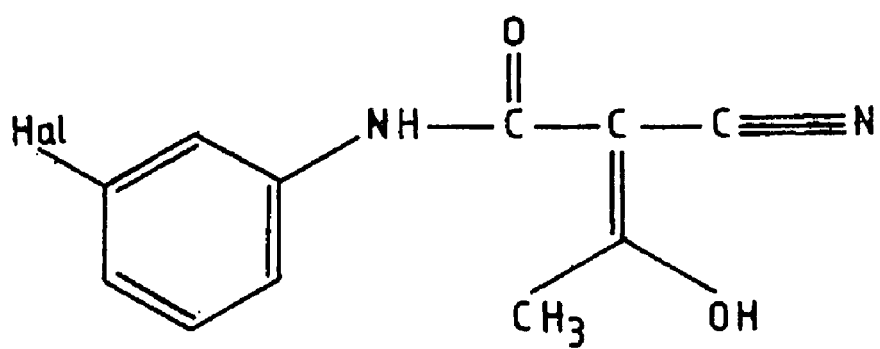
FIG. 2h is the structural formula of (2Z)-2-cyano-N-(3-halogenophenyl)-3-hydroxybut-2-enamide.
Figure 3A:
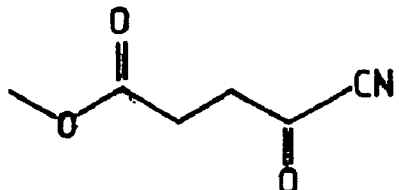
FIG. 3a is the structural formula of methyl 4-cyano-4-oxobutanoate.
Figure 3B:
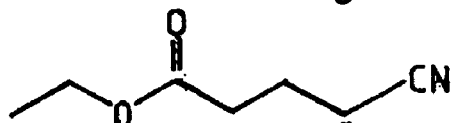
FIG. 3b is the structural formula of ethyl 4-cyano-4-oxobutanoate.
Figure 3C:
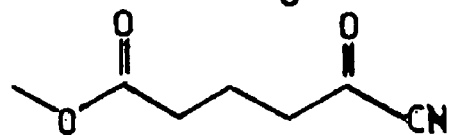
FIG. 3c is the structural formula of methyl 5-cyano-5-oxopentanoate.
Figure 3D:
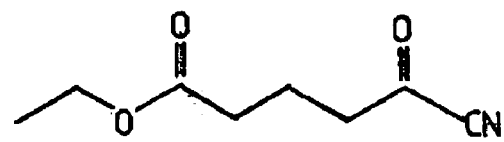
FIG. 3d is the structural formula of ethyl 5-cyano-5-oxopentanoate.
Figure 3E:
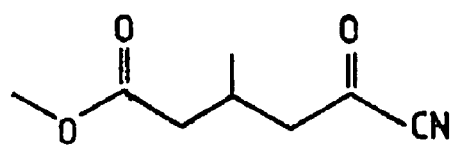
FIG. 3e is the structural formula of methyl 5-cyano-3-methyl-5-oxopentanoate.
Figure 3F:
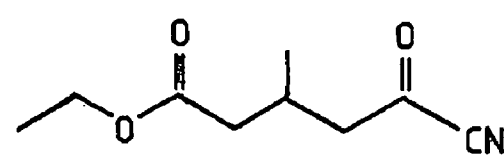
FIG. 3f is the structural formula of ethyl 5-cyano-3-methyl-5-oxopentanoate.
Figure 3G:
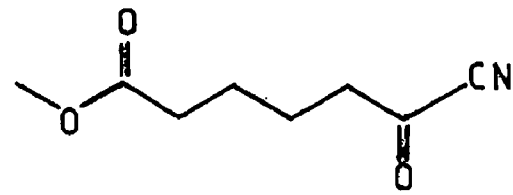
FIG. 3g is the structural formula of methyl 6-cyano-6-oxohexanoate.
Figure 3H:
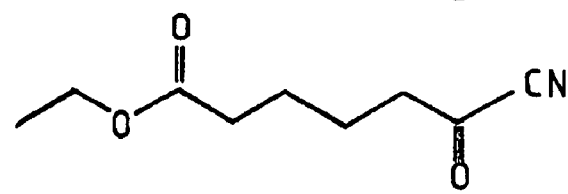
FIG. 3h is the structural formula of ethyl 6-cyano-6-oxohexanoate.
Figure 4A:
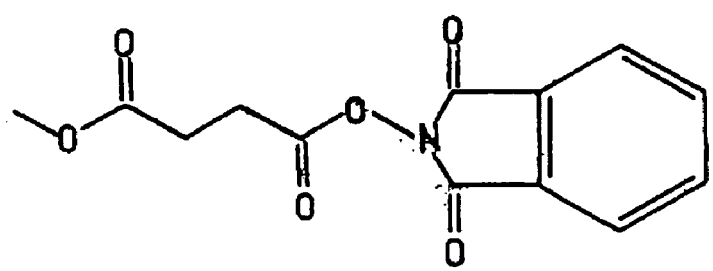
FIG. 4a is the structural formula of methyl 4-[(1,3-dioxo-1,3-dihydro-2H-isoindol-2-yl)oxy]-4-oxobutanoate.
Figure 4B:
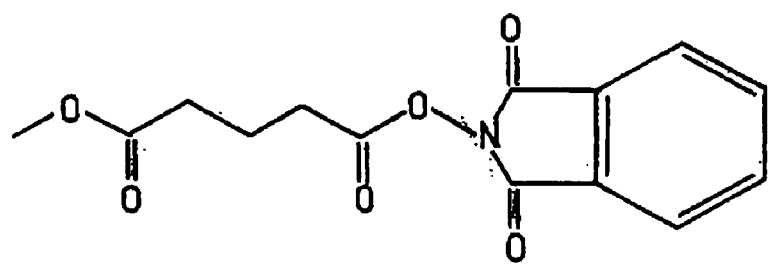
FIG. 4b is the structural formula of methyl 5-[(1,3-dioxo-1,3-dihydro-2H-isoindol-2-yl)oxy]-5-oxopentanoate.
Figure 4C:
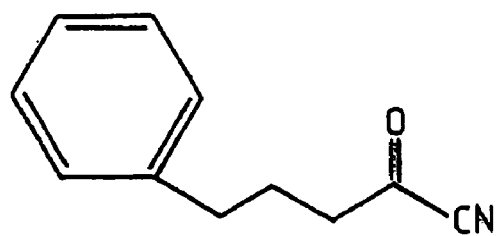
FIG. 4c is the structural formula of 2-oxo-5-phenylpentanenitrile.
Figure 5A:
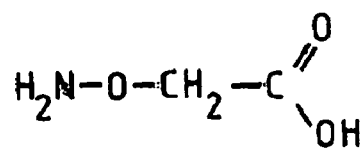
FIG. 5a is the structural formula of (aminooxy)acetic acid.
Figure 5B:
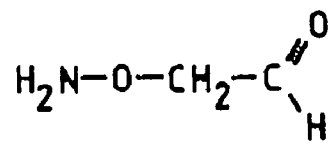
FIG. 5b is the structural formula of (aminooxy)acetaldehyde.
Figure 5C:
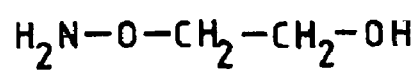
FIG. 5c is the structural formula of 2-(aminooxy)ethanol.
Figure 5D:
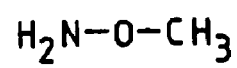
FIG. 5d is the structural formula of O-methylhydroxylamine.
Figure 5E:
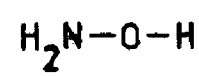
FIG. 5e is the structural formula of hydroxylamine.
Figure 5F:
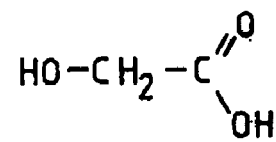
FIG. 5f is the structural formula of glycol acid.
Figure 5G:
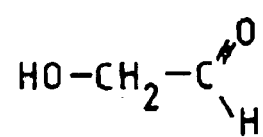
FIG. 5g is the structural formula of glycolaldehyde.
Figure 5H:
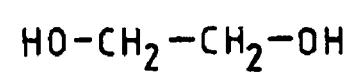
FIG. 5h is the structural formula of ethylene glycol.
Figure 5I:
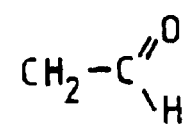
FIG. 5i is the structural formula of acetaldehyde.
Figure 6A:
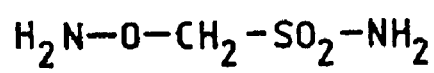
FIG. 6a is the structural formula of 1-(aminooxy)methanesulfonamide.
Figure 6B:
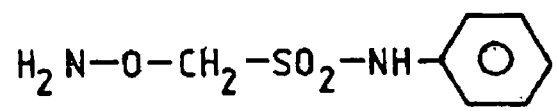
FIG. 6b is the structural formula of 1-(aminooxy)-N-phenylmethanesulfonamide.
Figure 6C:
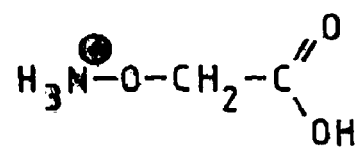
FIG. 6c is the structural formula of (carboxymethoxy) ammonium.
Figure 6D:
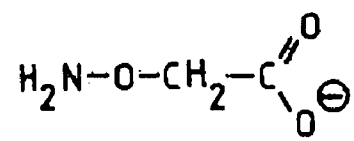
FIG. 6d is the structural formula of (aminooxy)acetate.
Figure 6E:
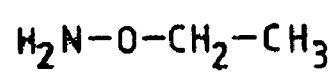
FIG. 6e is the structural formula of O-ethylhydroxylamine.
Figure 6F:
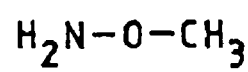
FIG. 6f is the structural formula of O-methylhydroxylamine.

The following explanations are independent from the above examples. The invention further teaches the use of N-(4'-trifluoromethylphenyl)-5-methylisoxazole-4-carboxamide ($C_{12}H_9F_3N_2O_2$; MW 270.2, see also FIG. 2a) and/or its natural active metabolites A 77 1726 according to FIG. 2b for preparing a pharmaceutical composition for treating tumor diseases, in particular solid tumors. The benzene ring may, alternatively to the shown substitution with —CF3, generally be singly, doubly, triply, quadruply or quintuply substituted with —Chal3 or —O-Chal3 or -Hal at an arbitrary position. The pharmaceutical composition according to the invention is particularly suited for treating large tumors, i.e. beginning from 0.1 to 1 $cm^3$ tumor size. A pharmaceutical composition according to the invention is for instance prepared for oral administration, for instance with the following auxiliary and carrier substances: colloidal $SiO_2$, crospovidone, hydroxypropylmethyl cellulose, lactose monohydrate, magnesium stearate, polyethylene glycol, povidone, starch, talcum, $TiO_2$ and/or yellow iron oxide. The dosage is 1 to 50 mg per day, preferably 10 to 30 mg. It may be recommended to administer in a therapy initially at a starting dose of 20 to 500 mg, in particular 50 to 150 mg, for the first 1 to 10 days, in particular the first 1 to 3 days. In another embodiment of the invention, the substance mentioned above is combined with one or several sugar phosphates, for instance fructose-1,6-biphosphate, glycerate-2,3-biphosphate, glycerate-3-phosphate, ribose-1,5-biphosphate, ribulose-1,5-biphosphate, and the combination of substances in a dosage form, for instance a tablet, may be mixed. It is however also possible to provide the components separately in identical or different dosage forms. The sugar phosphate may be administered in a dosage of 20 to 5,000 mg per day, for instance 100 to 500 mg.

These variants of the invention surprisingly lead to an inhibition of the growth of tumor cells and tumor tissue, since these substances or the metabolite can bind to the pyruvate kinase and inhibit or reverse the energy metabolism failing for tumor cells. From this situation there results a special advantage in that these substances specifically influence the metabolism of tumor cells and not or to a lower degree that of normal cells, and that there are thus only slight side effects if at all.

The effectivity of these substances is surprising because the known effect of a pyrimidine synthesis inhibitor relates to a completely different effective mechanism, and the phenomenological observation of an anti-proliferative effect is substantially directed toward immune cells and cells related to inflammatory diseases.

Of a special importance is a combination of one or several of the active ingredients mentioned on the previous page with one or several of the active ingredients mentioned further above or aminooxyacetate (AOA, NH2-O—CH2-COOH, salts or esters thereof, for instance C1–C10 alkyl or hydoxyalkyl esters). For instance AOA is particularly effective for small tumors (<0.1 to 1 $cm^3$) or prevents the development thereof, in particular development of metastases, whereas compounds of the formulas 10 or 11, if applicable in combination with sugar phosphate, is effective for the large tumors. The reason for this are the different metabolisms in small and large tumors. The above explanations for combinations apply in an analogous manner.

Substances according to the invention can further be used for preparing a pharmaceutical composition for treating heart insufficiency or the chronic cardiac failure (CCF). These are the variants defined by the New York Heart Association (NYHA) Classification or grades from NYHA I to NYHA IV. All these diseases are acute and/or chronic failure of the heart muscle to provide under load or even already at rest for the blood circulation or the transportation capacity required for the metabolism of the organism. The reasons are the insufficient glycolysis by glucose deficiency in the heart muscle and/or its insufficient oxygen supply and complex coronary inflammation processes (activation of cells of the immune system and complement). This aspect of the invention is based on the finding that by the substances according to the invention provide modulation of alternative energy-generating biochemical processes, and that is thus also possible to produce so to speak replacement pathways for the above insufficiently operating processes, for instance by activation of the serinolysis and glutaminolysis or to displace by substances according to the invention the existing dynamic balance between glycolysis on the one hand and glutaminolysis on the other hand in favor of the glycolysis, under simultaneous administration of oxygen (increase of the oxygen partial pressure in the blood, for instance by breathing). In this context, the administration of anti-inflammatory substances according to the invention can prevent the imminent highly dangerous acidosis (by lactate production). Compared to prior art measures, such as administration of ACE inhibitors, diuretics, digitalis, positive inotropic substances or isosorbide dinitrate, the substances according to the invention directly influence the energy metabolism, and the latter is improved. Side effects are as a consequence, comparatively weak.

In this context, it has been found by the invention that at least in the cases of the NYHA grade II to IV the concentration of tumor M2-PK (=M2-PK dimeric in contrast to standard M2-PK being tetrameric) in cells and/or the blood increases, which as a routine process can easily be determined, other than by the methods usual up to now. Therefore the invention further teaches the use of a tumor M2-PK detecting test system for preparing a diagnostic substance for the in vitro diagnosis of a heart insufficiency, in particular also of the grade or the inflammatory processes connected therewith. If for a patient increased M2-PK values (sick collective) are found in the blood plasma compared to standard values (defined maximum limits; normal collective), this is indicative for the existence of a heart insufficiency and/or for inflammatory processes correlated therewith, at least however for the risk to suffer from a heart insufficiency. Such a blood plasma analysis can easily and quickly be performed. Compared thereto, previous standard methods (gold standard, blood gas analysis) are not suitable for routine tests and are expensive. For this aspect of the invention, any known test systems can be used which detect tumor M2-PK, e.g. immunological test systems with antibodies. In particular, per se known test systems can be used which detect tumor M2-PK as a tumor metabolism marker, for instance monoclonal antibodies being specific herefor.

Various substances which can be used according to the invention are shown in the further figures, FIGS. 2a-2h, 3a-3h, 4a-4c, 5a-5i, and 6a-6f. In particular the essential variation possibilities are represented in an exemplary manner, the permutations which are easily deduced not being shown for the sake of simplicity. The invention finally also comprises all natural metabolites of the described substances.

We claim:
1. A compound according to formula I

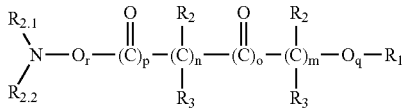

wherein R1=—H, —CN, —COO+, —COS+, —COOH, —COSH, —COOR1.1, —COSR1.1, N-phthalimidyl,
wherein R1=—H, C1–10 alkyl, C1–10 aralkyl or aryl,
wherein R2=—H, C1–C4 alkyl, —OR1.1, -Hal (—F—Cl, —Br, -J), —NR2.1R2.2, —Am, —O—Am, —S—Am,
wherein R3=—H, C1–C4 alkyl, —OR1.1, -Hal (—F—Cl, —Br, -J), —NR2.1R2.2, —Am, —O—Am, —S—Am,
wherein R2.1=—H, C1–10 alkyl, C1–10 aralkyl or aryl,
wherein R2.2=—H, C1–10 alkyl, C1–10 aralkyl or aryl,
wherein R2.1 and R2.2 may be identical or different,
wherein n and m may be identical or different and 0 to 10,
wherein o and p may be identical or different and 0 to 3,
wherein o>0, if n and m=0,
wherein R2 and R3 may be identical or different for Cn and/or Cm,
wherein R2 may be identical or different for every Cx=1 . . . n,
wherein R3 may be identical or different for every Cy=1 . . . m,
wherein —Am is an amino acid radical,
wherein q and r=0 or 1 and identical or different,
wherein —O$_r$— and/or —O$_q$— may also be replaced by —S$_r$— or —S$_q$—, resp.,
wherein —NR2.1R2.2 may be replaced by a linear or branched —C1–C20 alkyl, aralkyl or aryl,
wherein a group —CN, —(CO)—CN, —(CO)—O—R1 or —(CO)—R1 or —C—O—R1 may be replaced by —SO$_2$—NR2.1R2.2,
or a physiologically well tolerated salt of such a compound.

2. A compound according to claim 1, wherein R1=—CN.

3. A compound according to claim 1 or 2, wherein at least one of the R2 is —Am, wherein —Am preferably represents an amino acid radical of an essential amino acid, wherein in particular q=0 and r=1 or q=1 and r=0 or q=1 and r=1, m=1, R3=—H, n=o=p=0, R2.1=R2.2=—H.

4. A compound according to claim 1 or 2, wherein n=o=p=0, wherein m=0 to 4, wherein R2=R3=—H, or for at least one R2, R2=—Am, wherein R2.1=R2.2=—H, wherein q=0 and r=1.

5. A compound according to claim 1 or 2, wherein m=p=0, wherein o=1, wherein n=0 to 4, wherein R2=H, or for at least one R2, R2=—Am, wherein R3=—H or -Hal in the case Cx=1, wherein R3=—H for all Cx=n>1, wherein R2.1=R2.2=—H, wherein q=0 and r=1.

6. A compound according to claim 1 or 2, wherein m=1 to 4, wherein n=o=p=0, wherein R2=H, or for at least one R2, R2=—Am, wherein R3=—H or -Hal in the case Cy=1, wherein R3=—H for all Cy=m>1, wherein R2.1=R2.2=—H, wherein q=0 and r=1.

7. A compound according to claim 1 or 2, wherein o=p=1, wherein m=0, wherein n=0 to 4, wherein R2=R3=—H, or for at least one R2, R2=—Am, wherein R2.1=R2.2=—H, wherein q=0 and r=1.

8. A compound according to claim 1 or 2, wherein n=p=0, wherein o=1, wherein m=0 to 4, wherein R2=R3=—H, or for at least one R2, R2=—Am, wherein R2.1=R2.2=—H, wherein q=0 and r=1.

9. A compound according to claim 1 or 2, wherein m=p=0, wherein o=1, wherein n=1 to 4, wherein R2=R3=—H, or for at least one R2, R2=—Am, wherein R2.1=R2.2=—H, wherein q=0 and r=1.

10. A pharmaceutical composition, wherein a compound according to claim 1 is mixed with one or several physiologically well tolerated auxiliary substances and/or carrier substances and galenically prepared for local oral, or systemic administration comprising intravenous administration.

11. A method for inhibiting in vivo glycolysis or glutaminolysis of pyruvate kinase, asparaginase, serine dehydratases, transaminases, glutamate oxalacetate transaminase, glutamate pyruvate transaminase, glutamate dehydrogenase, malate dehydrogenase, desaminases or glutaminases in prokaryotes or eukaryotes comprising administering a pharmaceutical composition comprising the compound according to claim 1.

12. A method for treating multiple sclerosis comprising administering a pharmaceutical composition according to claim 10.

* * * * *